(12) United States Patent
Simmelink et al.

(10) Patent No.: US 10,280,532 B2
(45) Date of Patent: *May 7, 2019

(54) COLORED SUTURE

(71) Applicant: DSM IP ASSETS B.V., Heerlen (NL)

(72) Inventors: Joseph Arnold Paul Maria Simmelink, Cadier en Keer (NL); Claudia C. Vaz, Maastricht (NL)

(73) Assignee: DSM IP ASSETS B.V., Heerlen (NL)

( * ) Notice: Subject to any disclaimer, the term of this patent is extended or adjusted under 35 U.S.C. 154(b) by 281 days.

This patent is subject to a terminal disclaimer.

(21) Appl. No.: 15/338,085

(22) Filed: Oct. 28, 2016

(65) Prior Publication Data

US 2017/0044692 A1   Feb. 16, 2017

Related U.S. Application Data

(63) Continuation of application No. 12/599,869, filed as application No. PCT/EP2008/004135 on May 23, 2008, now Pat. No. 9,506,168.

(30) Foreign Application Priority Data

May 23, 2007   (EP) .................................... 07010217

(51) Int. Cl.
| | |
|---|---|
| *D01F 6/04* | (2006.01) |
| *A61L 17/04* | (2006.01) |
| *D01F 1/04* | (2006.01) |
| *D07B 1/02* | (2006.01) |
| *D01D 5/04* | (2006.01) |
| *D01D 5/06* | (2006.01) |
| *D02G 3/04* | (2006.01) |
| *C08L 23/06* | (2006.01) |

(52) U.S. Cl.
CPC ............ *D01F 6/04* (2013.01); *A61L 17/04* (2013.01); *C08L 23/06* (2013.01); *D01D 5/04* (2013.01); *D01D 5/06* (2013.01); *D01F 1/04* (2013.01); *D02G 3/04* (2013.01); *D07B 1/025* (2013.01); *D07B 2205/2014* (2013.01); *D10B 2509/04* (2013.01)

(58) Field of Classification Search
CPC ... A61L 17/04; D01F 1/04; D01F 6/04; D07B 1/025; D07B 2205/2014; D07B 2801/10; C08L 23/06
See application file for complete search history.

(56) References Cited

U.S. PATENT DOCUMENTS

| | | | | |
|---|---|---|---|---|
| 3,057,040 A | * | 10/1962 | Cuculo ..................... | D01F 6/60 428/401 |
| 3,166,073 A | * | 1/1965 | Kronenthal ............ | A61L 17/08 264/202 |
| 3,565,652 A | * | 2/1971 | Burnet ..................... | D01F 2/14 106/166.82 |
| 3,698,853 A | * | 10/1972 | Wilson .................... | A61L 17/08 606/229 |
| 4,008,303 A | * | 2/1977 | Glick ...................... | A61L 17/12 264/103 |
| 5,370,911 A | * | 12/1994 | Throne ................... | B05B 7/1404 427/185 |
| 5,373,911 A | | 12/1994 | Throne et al. | |
| 5,613,987 A | | 3/1997 | Kuroki et al. | |
| 5,651,377 A | * | 7/1997 | O'Donnell, Jr. ........................... | A61B 17/06166 128/898 |
| 6,060,007 A | * | 5/2000 | Hutton ..................... | D01F 1/04 264/103 |
| 2003/0050667 A1 | * | 3/2003 | Grafton ............ | A61B 17/06166 606/228 |
| 2004/0267313 A1 | * | 12/2004 | Amery ............. | A61B 17/06166 606/228 |
| 2005/0197417 A1 | * | 9/2005 | Sitzmann ............ | C03C 25/1045 522/64 |
| 2005/0208096 A1 | * | 9/2005 | Shalaby ................. | A61L 2/081 424/423 |
| 2006/0045899 A1 | * | 3/2006 | Sarangapani .......... | A01N 25/10 424/405 |
| 2006/0084745 A1 | * | 4/2006 | Kuhn ...................... | C08L 83/04 524/492 |
| 2006/0263432 A1 | * | 11/2006 | Yano .................... | A61K 9/5094 424/489 |
| 2007/0135840 A1 | * | 6/2007 | Schmieding ............ | A61L 17/10 606/228 |
| 2007/0154707 A1 | | 7/2007 | Simmelink et al. | |

(Continued)

FOREIGN PATENT DOCUMENTS

| | | |
|---|---|---|
| EP | 1 306 471 | 5/2003 |
| EP | 1 746 187 | 1/2007 |

(Continued)

OTHER PUBLICATIONS

International Search Report for PCT/EP2008/004135, dated Oct. 2, 2008.

(Continued)

*Primary Examiner* — Phong Son H Dang

(74) *Attorney, Agent, or Firm* — Nixon & Vanderhye P.C.

(57) ABSTRACT

Suture containing filaments of ultra-high molecular weight polyethylene (UHMwPE), characterized in that the suture contains a multi-filament yarn that is obtained by a process comprising the steps of:

a) Providing a mixture containing UHMwPE, a spinning solvent and a pigment b) Spinning a multi-filament yarn from the mixture by the gel spinning process.

9 Claims, No Drawings

(56) References Cited

U.S. PATENT DOCUMENTS

| | | | |
|---|---|---|---|
| 2008/0004702 A1* | 1/2008 | Denoziere | A61F 2/4405 623/17.13 |
| 2008/0009903 A1* | 1/2008 | Schmieding | C08L 71/00 606/228 |
| 2008/0021501 A1* | 1/2008 | Schmieding | A61L 17/10 606/228 |
| 2008/0027534 A1* | 1/2008 | Edwin | A61L 27/16 623/1.44 |
| 2008/0124368 A1* | 5/2008 | Sarangapani | A01N 25/10 424/405 |
| 2008/0287990 A1* | 11/2008 | Smit | D07B 1/025 606/228 |
| 2009/0012251 A1* | 1/2009 | Dirks | D01F 6/04 526/352 |
| 2009/0048628 A1* | 2/2009 | Marissen | A61B 17/06166 606/231 |

FOREIGN PATENT DOCUMENTS

| | | |
|---|---|---|
| EP | 1 847 276 | 10/2007 |
| GB | 879 069 | 10/1961 |
| WO | 2004/053212 | 6/2004 |
| WO | 2005/066401 | 7/2005 |

OTHER PUBLICATIONS

Thermoplast ® Blue 684, BASF Corourants for Plastics (Oct. 1998).

* cited by examiner

COLORED SUTURE

This application is a continuation of copending U.S. application Ser. No. 12/599,869, filed Jan. 14, 2010 (now U.S. Pat. No. 9,506,168), which is the national phase application of international application PCT/EP2008/004135, filed May 23, 2008, which designated the US and claims priority to European Application No. 07010217.3, filed May 23, 2007, the entire contents of each of which are hereby incorporated by reference.

The invention relates to a colored suture. The coloring of sutures is for example used to make the suture better contrast with the blood or tissue in the operating area. In complicated surgical operations, for example in arthroscopic surgery, when different suture ends are used in a small area, sutures of different color are used to assist surgeons in differing between the suture ends. It is also possible for this reason to combine filaments of different colors in a suture in a certain pattern, to aid surgeons in identifying the travel direction of the suture during surgery, particularly during arthroscopic operations.

Next to coloring is also suture strength an important consideration in selecting filaments for producing a suture. Very strong filaments, at present available for the production of sutures, are filaments of ultra-high molecular weight polyethylene (UHMwPE), produced according to the gel spinning process.

A problem of such filaments is that they are difficult to color. Due to the a-polar character of the UHMwPE a colorant like a dye or a colored coating material adheres poorly to the surface of the filament. If adhesion is insufficient the filaments may loose part or all of the colorant because of the handling during production of the sutures, or may loose part of the colorant in place in the human or animal body, which is undesired because of negative effects on the health. Attempts have been made to enhance the adhesion of colorants to the filaments by giving the filaments a pre-treatment, for example a plasma treatment. Such pre-treatments in general however have an adverse effect on the mechanical properties of the filaments, like for instance the tensile strength and often don't improve adhesion enough to make the filaments suitable to be used in sutures.

In another attempt filaments of UHMwPE were dyed using super critical carbon dioxide as a solvent for the dye, as disclosed in EP-A-0 873 445. In this case the dye penetrated in the body of the filament, so that adhesion problems did no longer play a role. However such a dye shows a tendency to leach out, which is unfavorable for application of the filaments in sutures. Also in U.S. Pat. No. 5,613,987 it was proposed to use a dye to color the UHMwPE filaments. Here the same problems occur.

Polyolefinic filaments, of which polypropylene filaments are the best example, are often colored by the incorporation of a pigment in the polymer composition of the filaments during extrusion of the filaments. In Prog. Polym. Sci. 27 (2002) 853-913 the process for pigmentation of polypropylene filaments is described.

The pigments are in a first step uniformly dispersed in a so-called carrier polymer to obtain a concentrated pre-mixture. In order to obtain a sufficient dispersion of the pigment the wetting of the pigment particles must be enhanced by the use of a low viscous carrier polymer and dispersants. A low viscous carrier polymer has a negative influence on mechanical properties of the UHMwPE filaments. Furthermore such filaments have a very low diameter compared to the diameter of polypropylene filaments, so that un-dispersed or re-agglomerated clumps of pigment particles will have a detrimental effect on the tensile strength of the filaments. Therefore it is disadvised in U.S. Pat. No. 5,613,987 to use pigments in UHMwPE filaments. Also the use of dispersants in filaments that are used in sutures is disadvantages, because such filaments must be biocompatible and dispersants have a negative effect on that.

One solution proposed to overcome the problems of the coloring of filaments of UHMwPE is to combine the filaments in a suture with filaments of a different polymer, preferably nylon, as disclosed in U.S. Pat. No. 7,029,490. Such sutures however have a complicated structure and the nylon filaments only contribute to the strength of the suture at a lower level compared to the filaments of UHMwPE.

Object of the invention is to provide a colored suture, which suture does not show the problems described above.

Surprisingly such a suture is obtained if the suture contains a multi-filament yarn that is obtained by a process comprising the steps of:
a) Providing a mixture containing UHMwPE, a spinning solvent and a pigment
b) Spinning a multi-filament yarn from the mixture by the gel spinning process.

The preparation of filaments of ultra high molecular weight polyethylene (UHMWPE) filaments, prepared by a gel spinning process, is for example described in EP 0205960 A, EP 0213208 A1, U.S. Pat. No. 4,413,110, GB 2042414 A, EP 0200547 B1, EP 0472114 B1, WO 01/73173 A1, and Advanced Fiber Spinning Technology, Ed. T. Nakajima, Woodhead Publ. Ltd (1994), ISBN 1-855-73182-7, and references cited therein. Gel spinning is understood to include at least the steps of spinning filaments from a solution of ultra-high molecular weight polyethylene in a spin solvent; cooling the filament obtained to form a gel filament; removing at least partly the spin solvent from the gel filament; and drawing the filament in at least one drawing step before, during or after removing spin solvent. Suitable spin solvents include for example paraffin's, mineral oil, kerosene or decalin. Spin solvent can be removed by evaporation, by extraction, or by a combination of evaporation and extraction routes. Such filaments are commercially available as Spectra® or Dyneema® grades.

Good results are obtained if the UHMWPE has an intrinsic viscosity (IV, as determined according to method PTC-179 (Hercules Inc. Rev. Apr. 29, 1982) at 135° C. in decalin, with dissolution time of 16 hours, with anti-oxidant DBPC in an amount of 2 g/l solution, and the viscosity at different concentrations extrapolated to zero concentration) of above 5 dl/g. Particularly suitable is UHMWPE with IV of between about 8 and 40 dl/g, more preferably between 10 and 30, even more preferably between 12 and 28, most preferably between 15 and 25 dl/g. These ranges represent an optimum in polymer processability and filament properties. Intrinsic viscosity is a measure for molar mass (also called molecular weight) that can more easily be determined than actual molar mass parameters like $M_n$ and $M_w$. There are several empirical relations between IV and $M_w$, but such relation is highly dependent on molar mass distribution. Based on the equation $M_w = 5.37 \times 10^4 [IV]^{1.37}$ (see EP 0504954 A1) an IV of 8 dl/g would be equivalent to Mw of about 930 kg/mol.

Preferably, the UHMWPE is a linear polyethylene with less than one branch per 100 carbon atoms, and preferably less than one side chain per 300 carbon atoms, a branch usually containing at least 10 carbon atoms. The linear polyethylene may further contain up to 5 mol % of one or more comonomers, such as alkenes like propylene, butene, pentene, 4-methylpentene or octene.

In a preferred embodiment, the UHMWPE contains a small amount of relatively small groups as side chains, preferably a C1-C4 alkyl group. It is found that a filament from UHMWPE with a certain amount of such groups show reduced creep behaviour. Too large a side chain, or too high an amount of side chains, however, negatively affects the processing and especially the drawing behaviour of the filaments. For this reason, the UHMWPE preferably contains methyl or ethyl side chains, more preferably methyl side chains. The UHMWPE therefore contains preferably at least 0.2, more preferably at least, still more preferably at least 0.3, still more preferably at least 0.4, most preferably at least 0.5 methyl or ethyl side chains. The amount of side chains is preferably at most 20, more preferably at most 10 per 1000 carbon atoms.

The UHMwPE can be a single polymer grade, but also a mixture of two or more different grades, e.g. differing in IV or molar mass distribution, and/or number of side chains. Preferably the polymeric part of the filaments is a single grade UHMwPE.

The number of filaments in the multi-filament yarn may be between 10 and 1000. Preferably the number of filaments in the multi-filament yarn is more than 20, more preferably more than 30.

The mixture containing the UHMwPE, the spinning solvent and the pigment may be provided at different stages in the gel spinning process. It is for example possible to produce in a first step a dry mixture of UHMwPE powder and the pigment, to produce in a second step a slurry of that mixture in a spinning solvent, to dissolve the UHMwPE in the spinning solvent in a third step to obtain a slurry of the pigment in a solution of UHMwPE in the spinning solvent and to spin the multi-filament yarn from that solution. It is also possible to produce a solution of UHMwPE in the spinning solvent first and to add the pigment to that solution.

The UHMwPE filaments preferably contain less than 800 ppm of residual amounts of spin solvent, more preferably less than 500, even more preferably less than 250, most preferably less than 100 ppm, such as less than 80 ppm, or less than 60 ppm. Filaments and suture with low residual amount of spin solvent is highly advantageous in being more suitable for implantation.

Suitable pigments include organic and inorganic pigments. Examples of organic pigments include azo-pigments and phtalo-pigments. Good results are obtained with C.I. Vat brown I and C.I. Solvent Yellow 18. Examples of inorganic pigments include pigments containing titanium dioxide, iron oxides and chromium oxides. Good results are obtained with aluminium-chromium-cobalt oxide, since a suture with good mechanical properties and a low degree of leaching out is obtained.

The amount of pigment used may be between 0.1-7 wt. % of the final filament, as used for the production of the suture. Preferably the final filament contains at least 0.3 wt. %, more preferably at least 0.5 wt. % even more preferably at least 0.7 wt. % of pigment. Preferably the final filament contains at most 5.0 wt. %, more preferably at most 3 wt. % of pigment, even more preferably at least 2.5 wt. %, most preferably at most 2 wt. %. This is in view of obtaining a bright colour and good mechanical properties.

The UHMwPE filaments in the suture according to the invention consist preferably of UHMwPE, the pigment and less than 1000 ppm of further constituents, preferably less than 500 ppm of further constituents, more preferably less than 200 ppm of further constituents, most preferably less than 100 ppm of further constituents, such as less than 80 ppm, or less than 60 ppm.

A suitable size for the suture according to the invention may be in the full USP range for sutures (e.g. 12-0 to 10). A USP value of 10 corresponds with a maximum diameter of 1.3 mm. In one preferred embodiment the suture member has a titer of between 25 and 500 dtex. In that case the suture is very suitable for cardiovascular operations. In another preferred embodiment the suture has a titer of between 500 and 3000 dtex. In that case the suture is very suitable for use in orthopaedic applications. In yet another preferred embodiment the suture has a titer of between 3000 and 9000 dtex. In that case the suture is very suitable to be used in heavy orthopaedic applications.

The suture may in addition to the ultra high molecular polyolefin filaments comprise further components, for example compounds that provide some functional effect, like anti-microbial or anti-inflammatory action, or that further improve knotting performance. The amount of such other components is generally limited to at most 20 mass % (relative to total cable mass), preferably at most 10, more preferably at most 5 mass %.

The suture according to the invention comprises preferably at least 50 mass % of the ultra high molecular weight polyolefin filaments. The ultra high molecular weight polyolefin filaments contribute most to the strength properties of the member. Furthermore the filaments enhance the sliding properties of the suture through tissue. Therefore more preferably the suture comprises at least 60 mass % of the ultra high molecular weight polyolefin filaments, more preferably at least 70, 80 or at least 90 mass %. The suture may further comprise other fibres, e.g. other biocompatible materials like polymers, to provide some other additional properties to the suture, including improved knot slip behaviour or visual contrast. Such other fibres may be present in the form of one or more strands in the suture. However, preferably each strand has the same composition, so that each strand comprises the same amount of the polyolefin filaments and of the other filaments. This ensures that the suture has a homogeneous structure.

Suitable examples of other fibrous materials include filaments or staple fibres made from non-absorbable polymers like other polyolefin's, fluoropolymers, or semi-aromatic polyesters like polyethylene terephthalate, absorbable polymers like aliphatic polyesters based on e.g. lactides.

Most preferably the suture consists of the polyolefin filaments.

The invention also relates to the use of the suture according to the invention in surgical method.

The invention is further explained in the examples, without being limited to the examples.

Methods

Intrinsic Viscosity.

The Intrinsic Viscosity (IV) is determined according to method PTC-179 (Hercules Inc. Rev. Apr. 29, 1982) at 135° C. in decalin, the dissolution time being 16 hours, with DBPC as anti-oxidant in an amount of 2 g/l solution, by extrapolating the viscosity as measured at different concentrations to zero concentration;

Tensile Properties.

Tensile properties: tenacity, tensile modulus (or modulus) and elongation at break (or eab) are defined and determined on multifilament yarns with a procedure in accordance with ASTM D885M, using a nominal gauge length of the fibre of 500 mm, a crosshead speed of 50%/min and Instron 2714 clamps, of type Fibre Grip D5618C. On the basis of the measured stress-strain curve the modulus is determined as the gradient between 0.3 and 1% strain. For calculation of the modulus and strength, the tensile forces measured are divided by the titre, as determined by weighing 10 meters of fibre; values in GPa are calculated assuming a density of 0.97 g/cm$^3$;

Leaching Tests

According to the requirements of ISO 10993-12:2002(E) an extraction was performed with samples of multi-filament yarn in both polar (distilled water) and non-polar (cotton-seed oil) solvents. The extraction conditions were 37° C. for 24 and 72 hours.

After dilution with acetonitrile, the different phases were analyzed on the presence of pigment using Liquid Chromatography-Mass Spectrometry (LC-MS) and Gas Chromatography-Mass Spectrometry (GC-MS). In case no leaching I was observed means that leaching was lower than 10 ppb.

Cytotoxicity.

Cytotoxicity tests were performed according to ISO 10993-5, 1999: Biological Evaluation of Medical Devices—Part 5: Tests for in vitro cytotoxicity. The biological reactivity of a mammalian monolayer, L929 mouse fibroblast cell culture, in response to the test item extracts (samples containing up to 2.0 wt. % pigment) was determined. Extracts were prepared at 37° C. (±1) for 24 hours in a humidified atmosphere containing 5±1% $CO_2$. Positive (natural rubber) and negative (silicone) control articles were prepared to verify the proper functioning of the test system. The maintenance medium of the cell cultures was replaced by the extracts of the tests item or control article in triplicate and the cultures incubated for 48 hours, at 37° C. (±1). Biological reactivity was rated on the following scale:
  grade 0 (no reactivity)
  grade 1 (slight reactivity)
  grade 2 (mild reactivity)
  grade 3 (moderate reactivity)
  grade 4 (severe reactivity)

EXAMPLES 1-4

Slurries containing decalin, 6 mass % of powder of UHMwPE having an IV of 14 and 0.5, 1, 1.5 respectively 2 wt. % of aluminum-chromium-cobalt oxide pigment (of the cations is 32.5% Co, 32% Al and 35.5 Cr) were prepared in a mixer.

The slurries were fed to a twin screw extruder having a diameter of 25 mm, being equipped with a gear-pump at a temperature setting of 180° C. In the extruder the UHMwPE was dissolved in the decalin and the so obtained mixture of the UHMwPE dissolved in the decalin and the pigment was extruded through a spin plate having 24 spin holes into a nitrogen atmosphere with a rate of 1.0 g/min per hole. The so obtained solution filaments were cooled in a water bath kept at about 35° C. and with a water flow rate of about 5 cm/s perpendicular to the filaments entering the bath, and taken-up at such rate that a draw ratio of 15 was applied to the as-spun filaments in the air-gap of 15 mm. The filaments subsequently entered an oven at 130° C. The filaments were further stretched, during which process the decalin evaporated from the filaments. After the stretching process the filaments were kept taut in an oxygen free environment for 24 hours at 100° C.

Mechanical properties, leaching out and cytotoxicity were determined on the so obtained multi-filament yarns.

The mechanical properties are reported in table 1. Favourable mechanical properties were obtained.

No compounds related to pigment, or other unknown compounds, where found. The pigment <10 μg/kg (<10 ppb).

From these results it can be concluded that the bio-availability of pigment due to leaching from sutures according to the invention containing the multi-filament yarn is negligible.

All the extracts of the colored samples when submitted to the cytotoxicity test exhibited no reactivity (grade 0) by the cell cultures. Severe reactivity (grade 4) was observed for the positive control article. The negative control article showed no signs of reactivity (grade 0). Therefore it can be concluded that sutures according to the invention containing the multi-filament yarn are non-cytotoxic.

The yarns furthermore show a homogeneous and bright colour.

Comparative Test A

Multi-filament yarn was produced according to examples 1-4, however no pigment was used.

The multi-filament yarn was dyed with D&C blue No 6 (delivered by Sigma Aldrich of the USA) by placing the multi-filament yarn for 7 hours at 120° C. in a solution of the dye in super-critical carbon dioxide.

The resulting yarns presented a non-homogeneous color distribution pattern.

Mechanical properties and leaching out were determined.

Mechanical properties are reported in table 1. A serious decline in mechanical properties was observed (tenacity decreased about 40%).

Considerable leaching out took place in coconut oil as was already clear from the disappearing color of the multi-filament yarn.

From these results it is clear that sutures containing the multi-filament yarn according to comparative test A are not suitable for use in surgery.

Comparative Test B

Multi-filament yarn was produced according to examples 1-4, however no pigment was used.

The multi-filament yarn was dip-coated with a polyurethane coating containing an azo-dye (Sudan Red D, delivered by Sigma Aldrich).

Test data of the multi-filament yarn were measured and reported in table I. It is clear that considerable leaching out took place and that the cyto-toxicity of the filaments is insufficient. Therefore sutures containing the multi-filament yarn according to comparative test B are not suitable for use in surgery.

TABLE 1

| Example/ Xomp. exp. | Tenacity [cN/ dTex] | Modulus [cN/ dTex] | Eab [%] | leaching [-] | cytotox. [-] | colouring [-] |
|---|---|---|---|---|---|---|
| I | 37 | 1439 | 2.8 | No | 0 | homogeneous |
| II | 37 | 1377 | 2.9 | No | 0 | Homogeneous |
| III | 40 | 1501 | 3.0 | No | 0 | Homogeneous |
| IV | 37 | 1414 | 2.9 | No | 0 | Homogeneous |
| A | 21 | — | — | Yes | — | In-homogeneous |
| B | 37 | 1381 | 2.8 | Yes | — | In-homogeneous |

The invention claimed is:
1. A colored multi-filament yarn comprising filaments that have been obtained by gel spinning a mixture containing ultra-high molecular weight polyethylene (UHMwPE) having an intrinsic viscosity (IV) of between about 8 and 40 dl/g, a spin solvent and a pigment, and wherein the filaments consist of UHMwPE, between 0.1 and 7.0 wt. % of an inorganic chromium oxide-containing pigment, a residual amount of spin solvent of less than about 500 ppm, and less than 1000 ppm of further constituents.

2. The multi-filament yarn according to claim 1, wherein the amount of the inorganic pigment present in the filaments is between 0.3 and 5.0 wt. %.

3. The multi-filament yarn according to claim 1, wherein the amount of the inorganic pigment present in the filaments is lower than 2.0 wt. %.

4. The multi-filament yarn according to claim 1, wherein the inorganic pigment is aluminum-chromium-cobalt oxide.

5. The multi-filament yarn according to claim 1, wherein the residual amount of spin solvent is less than 250 ppm.

6. The multi-filament yarn according to claim 1, wherein the residual amount of spin solvent is less than 100 ppm.

7. The multi-filament yarn according to claim 1, wherein the residual amount of spin solvent is less than 60 ppm.

8. The multi-filament yarn according to claim 1, wherein the filaments contain less than 500 ppm of further constituents.

9. The multi-filament yarn according to claim 1, wherein the number of filaments is between 10 and 1000.

\* \* \* \* \*